United States Patent
Bennett et al.

(10) Patent No.: US 10,750,989 B2
(45) Date of Patent: *Aug. 25, 2020

(54) MRI-BASED SYSTEMS AND METHODS FOR DETERMINING FUNCTION CAPACITY OF THE KIDNEY

(71) Applicant: NEPHRODIAGNOSTICS LLC, Clayton, MO (US)

(72) Inventors: Kevin Michael Bennett, St. Louis, MO (US); Scott Charles Beeman, St. Louis, MO (US)

(73) Assignee: Nephrodiagnostics LLC, Clayton, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/378,117

(22) Filed: Apr. 8, 2019

(65) Prior Publication Data

US 2019/0298247 A1 Oct. 3, 2019

Related U.S. Application Data

(63) Continuation of application No. 14/742,272, filed on Jun. 17, 2015, now Pat. No. 10,251,592.

(60) Provisional application No. 62/012,992, filed on Jun. 17, 2014.

(51) Int. Cl.
| | | |
|---|---|---|
| *A61B 5/00* | (2006.01) | |
| *A61K 49/14* | (2006.01) | |
| *A61B 5/20* | (2006.01) | |
| *A61B 5/055* | (2006.01) | |
| *G01R 33/56* | (2006.01) | |

(52) U.S. Cl.
CPC ............. *A61B 5/201* (2013.01); *A61B 5/055* (2013.01); *A61B 5/4222* (2013.01); *A61K 49/14* (2013.01); *G01R 33/5601* (2013.01); *G01R 33/5608* (2013.01)

(58) Field of Classification Search
CPC .. A61B 5/00; A61B 5/055; A61B 5/20; A61K 49/00; A61K 49/14
See application file for complete search history.

(56) References Cited

U.S. PATENT DOCUMENTS 7,319,328 B1 * 1/2008 Karmonik ........ G01R 33/56341
324/309

* cited by examiner

*Primary Examiner* — Michael G. Hartley
*Assistant Examiner* — Jagadishwar R Samala
(74) *Attorney, Agent, or Firm* — Armstrong Teasdale LLP (57) ABSTRACT

Systems and methods for noninvasively determining the function capacity of the kidney are provided. In the methods, first contrast agent is injected into the vasculature of a subject. The contrast agent is to be bound with functioning glomeruli of the kidney of the subject. Then, the kidney is imaged with a magnetic resonance imaging (MRI) system to acquire MRI images of the kidney. In the images, signal magnitudes or phases of voxels of regions bound with the contrast agent are different from signal magnitudes or phases of voxels of regions not bound with the contrast agent. Afterwards, the function capacity of the kidney is determined using the MRI images. Lastly, a report of the function capacity of the kidney is generated.

20 Claims, 9 Drawing Sheets

MRI-BASED SYSTEMS AND METHODS FOR DETERMINING FUNCTION CAPACITY OF THE KIDNEY

CROSS REFERENCE

This application is continuation application of U.S. Non-Provisional application Ser. No. 14/742,272 filed on Jun. 17, 2015, which claims priority to, and incorporates herein by reference in its entirety, U.S. Provisional Patent Application Ser. No. 62/012,992, filed on Jun. 17, 2014, the disclosures of which are hereby incorporated by reference in their entirety.

STATEMENT REGARDING FEDERALLY-SPONSORED RESEARCH

This invention was made with government support under DK-091722 awarded by the National Institutes of Health. The government has certain rights in the invention.

BACKGROUND

Chronic kidney disease (CKD) affects 1 in 10 American adults and its prevalence is rapidly increasing. In the United States alone, 90,000 patients will die from end stage renal disease (ESRD) each year, and over $40 billion is spent on treatment of CKD and ESRD. While most of the burden of CKD is focused on ESRD, even the mild stages of CKD are not benign and result in both higher risks of cardiovascular disease and increased health care costs.

Glomeruli, the functioning structure of nephrons, can lose their function due to high blood pressure, disease affecting the kidney, and other attributes of health. It is now well known that lower number of functioning nephrons are associated with higher susceptibility to kidney disease and hypertension. A low number or a loss of nephrons leads to glomerular hypertrophy and hyperfiltration. The theory behind this is that a kidney with a low number of nephrons must filter the same amount of fluid per unit time as a kidney with high nephron number, and therefore to maintain an acceptable total filtration surface area and a constant glomerular filtration rate (GFR), each glomerulus in a poorly endowed kidney must grow larger and filter more fluid than its healthy counterpart. While this likely compensatory mechanism may maintain homeostasis in the early stages, it complicates the use of GFR measurements for early detection of kidney diseases involving changes in nephron number and glomerular volume. Ideally, clinical measurements of glomerular number and volume can be used to detect and monitor loss of nephrons and glomerular hypertrophy in patients at risk of CKD, such as those with diabetes and hypertension.

Currently, measurements of total nephron number ($N_{glom}$) and mean glomerular volume ($V_{glom}$) require histological sectioning and quantitation of a fraction of a kidney and extrapolation to a total glomerular number and volume. Studies employing these methods have provided significant insights into renal physiology and the role of Nom and $V_{glom}$ in both kidney-specific and systemic diseases. Unfortunately, these methods require resection and destruction of the kidney. At this time, there are no methods available for direct measurements of $N_{glom}$, $V_{glom}$, or protein leakage of individual glomeruli in vivo. Such methods would provide a window for early intervention and may also prove vital in assessing renal allograft viability prior to transplant.

Therefore, it would be desirable to have a system and method for detecting and monitoring kidney function capacity noninvasively and at early stages.

SUMMARY

The present disclosure overcomes the aforementioned drawbacks by providing systems and methods for noninvasively detecting the function capacity of the kidney. Cationized ferritin can be used as contrast agent to label functioning glomeruli. The voxels associated with labeled glomeruli have different signal magnitudes or phases due to the contrast agent compared to those of unlabeled structure in the kidney. The magnetic resonance images of the labeled kidney can be used to determine the function capacity of the kidney such as the apparent volumes and number of the functioning glomeruli.

In accordance with one aspect of the disclosure, a method for noninvasively determining the function capacity of the kidney is provided. In the method, first contrast agent is injected into the vasculature of a subject. The contrast agent is to be bound with functioning glomeruli of the kidney of the subject. Then, the kidney is imaged with a magnetic resonance imaging (MRI) system to acquire MRI images of the kidney. In the images, signal magnitudes or phases of voxels of regions bound with the contrast agent are different from signal magnitudes or phases of voxels of regions not bound with the contrast agent. Afterwards, the function capacity of the kidney is determined using the MRI images. Lastly, a report of the function capacity of the kidney is generated.

In accordance with another aspect of the disclosure, a magnetic resonance imaging (MRI) system is disclosed that includes a magnet system configured to generate a polarizing magnetic field about at least a portion of a subject arranged in the MRI system and a magnetic gradient system including a plurality of magnetic gradient coils configured to apply at least one magnetic gradient field to the polarizing magnetic field. The MRI system also includes a radio frequency (RF) system configured to apply an RF field to the subject and to receive magnetic resonance (MR) signals therefrom and a computer system. The computer system is programmed to first inject contrast agent into vasculature of a subject. The contrast agent is to be bound with functioning glomeruli of the kidney of the subject. Then, the kidney is imaged with a magnetic resonance imaging (MRI) system to acquire MRI images of the kidney. In the images, signal magnitudes or phases of voxels of regions bound with the contrast agent are different from signal magnitudes or phases of voxels of regions not bound with the contrast agent. Afterwards, the function capacity of the kidney is determined using the MRI images. Lastly, a report of the function capacity of the kidney is generated.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2F shows the transmission electron microscopy of the naive control kidney in FIG. 2D. In FIGS. 2A-2F, white scale bars=50 μm and black scale bars=0.2 μm.

FIG. 4C shows histopathology performed on the cortical regions of the kidney marked by the bottom arrow in FIG. 4A. In FIGS. 4B and 4C, scale bars=400 μm.

FIG. 5. Immunofluorescence of intravenous CF labeling and histopathology in human donor kidneys. Triple immunofluorescence with an antibody against Wilms Tumor 1 antigen (WT-1) as a marker of healthy mature podocytes (green), ferritin as a marker of injected CF (red) and DAPI as a nuclear marker (blue). A-D shows a normal glomerulus from patient CF3 with strong podocyte labeling and strong ferritin labeling on the GBM and fine ferritin labeling in peritubular capillaries and Bowman's capsule. E-H shows a glomerulus with reduced ferritin labeling in the tuft, and ferritin signal on Bowman's space (very frequent in CF2, regular in CF1 and very rare in CF3). I-L shows two pathological glomeruli. On the left, a glomerulus with expanded Bowman's space, collapsed tuft and WT-1 positive cells on Bowman's capsule: all three features are suggesting an atubular glomerulus or obstructed collecting ducts. On the right (dashed ellipsis), a collapsed glomerular tuft without open capillaries and indirect signs of glomerulosclerosis. M shows a normal glomerulus (present in all subjects; very frequent in CF3). N shows a glomerulus with ferritin "leakage" into the Bowman's space (frequent finding in CF1 and CF2). O shows a normal vessel (frequent finding in CF3). P shows a vessel with vascular remodeling (very common in CF2, and sporadic finding in CF1). White arrowheads (e.g., those in FIG. 6, C, D, G, H, M, N, O, and P) represent ferritin labeling outside the glomerular tuft, green arrowheads (e.g., those in FIG. 6, L) show WT-1 expression in cells on Bowman's capsule. Scale bars=50 μm.

FIG. 6. Glomeruli are made visible in all three CF-labeled kidneys (A, D, G) and the glomerular segmentation algorithm was able to identify, count, and measure the volume of labeled glomeruli (B, E, H). Identified glomeruli are assigned an arbitrary color for visualization purposes in these panels. The majority of regions defined as glomeruli by the algorithm exist in the cortical and juxtamedullary regions of the representative slice. The control kidney (J, K) shows very few regions defined as 'glomeruli'—most of which are likely attributed to residual blood. The MRI-measured apparent glomerular volume ($aV_{glom}$) distribution for each kidney is shown, along with a grey line showing the median MRI-measured $aV_{glom}$ and a black line showing the $V_{glom}$ estimate obtained using stereology (C, F, I, and L). Note that no stereological measurement is available for the control kidney.

FIG. 7. Line profiles (16 per kidney) were drawn through the cortex of each CF-labeled kidney in 7T MRI volumes (all of which have the same field of view (FOV) and matrix size). Here the line signal profiles of the solid white profiles are plotted (A, C, and E) and the mean power spectrum for the 16 line profiles are shown (B, D, and F). Black traces are data from CF-labeled kidneys and grey traces are data from the naive control. Arrows point to spatial spectral peaks of particular interest. Qualitatively, the line profiles for the CF-labeled kidneys appear different from one another, with the CF3 line profiles being mostly composed of relatively high frequency oscillations, the CF2 oscillations being mostly composed of relatively low frequency oscillations, and the CF1 kidney being composed of a mixture of high and low frequency components. The line profile signal changes associated with the appearance and disappearance of sites of CF accumulation in the CF1 kidney correspond to two spectral peaks; one at k=0.8 mm$^{-1}$ (4.5% of total signal) and one at k=1.2 mm$^{-1}$ (5% of total signal) (B). The line profile signal changes associated with CF accumulation in the CF2 kidney correspond to only a low frequency spatial signal oscillation at k=0.8 mm$^{-1}$ and account for 5% of the total signal along the line profiles (D). The line profile signal changes associated with the accumulation of CF in the CF3 kidney correspond only to high frequency spatial oscillations between k=1.2 and 1.5 mm$^{-1}$ which account for 10% of the total signal along the line profiles (F). Histopathology showed that CF2 had substantial nephrosclerosis, CF1 had mild nephrosclerosis, and CF3 had minimal nephrosclerosis; therefore the prominence of low frequency spectral peaks may suggest the advancement of nephrosclerosis. Stars represent a statistically significant difference between the CF-labeled kidney and the naive control (p<0.04) and arrows denote peaks of particular interest. Error bars represent mean±one standard deviation between power spectra of sixteen randomly chosen line profiles.

DETAILED DESCRIPTION

Glomerular morphology can be noninvasively measured with a magnetic resonance imaging (MRI) contrast agent that specifically targets the glomerular basement membrane (GBM). The cationized ferritin nanoparticle (CF) can be used as an intravenous MRI contrast agent to detect functional structures in fenestrated organs, including kidney glomeruli. The application of CF in the kidney is based on electrostatic binding of CF to anionic proteoglycans of the GBM, allowing each perfused glomerulus in the kidney to be located, counted, and measured using MRI. The systems and method as disclosed herein can also be used to detect glomerular permeability to macromolecules of focal and segmental glomerulosclerosis. MRI, after CF injection, also enables measurements of glomerular volume distributions and pathologies in the kidney. Because it is naturally occurring in mammalian tissue, CF may be relatively nontoxic.

Figure 1:
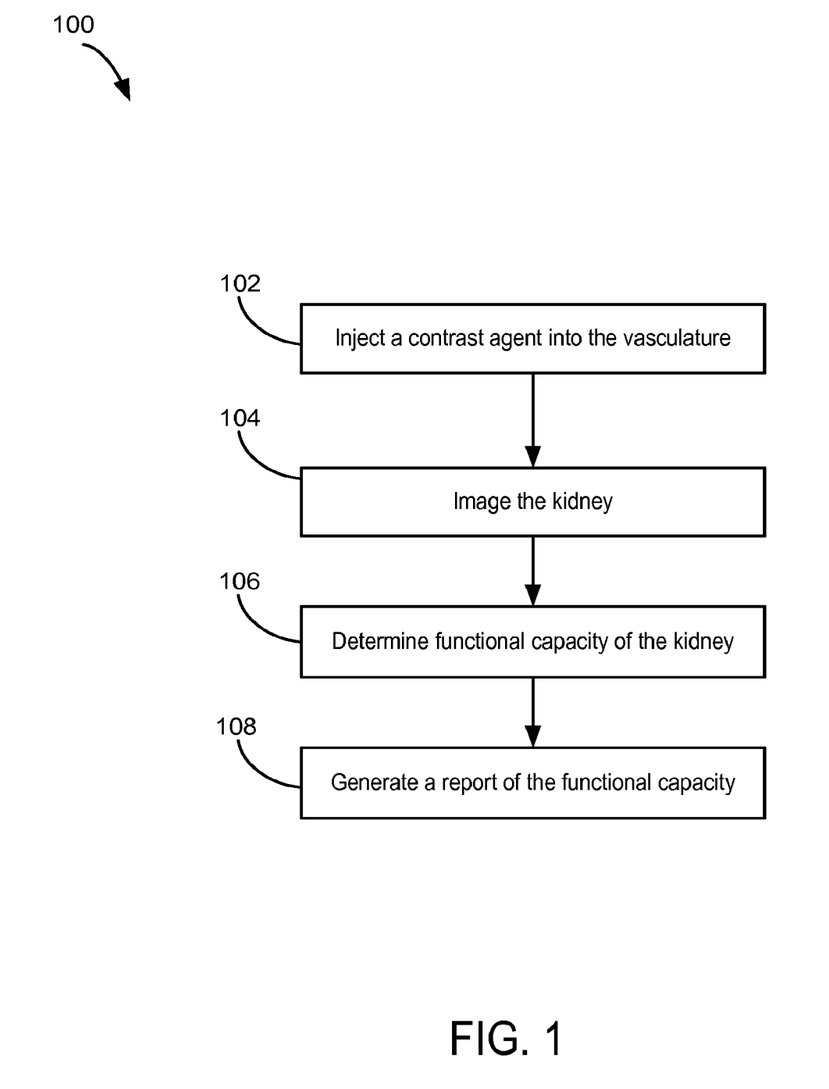
FIG. 1 is a flow chart setting forth the steps of one, non-limiting example of a method for detecting function capacity of the kidney.

Referring to FIG. 1, a flowchart 100 of an example method implemented according to the present disclosure is provided. In step 102, a contrast agent is into vasculature of a subject. A subject can be a human (live or deceased), an animal (live or deceased), or part of a human or an animal that includes the kidney. The contrast agent binds to functioning glomeruli in the kidney of the subject. The contrast agent can comprise apoferritin filled with a metal, a radio label, or a fluorescent molecule, where the apoferritin targets the functioning glomeruli using cationic surface charge. Apoferritin can be from multiple sources. It can be bacterial, mammalian, or from any species of mammal. It can be a recombinant human version and be cationizied. A person skilled in the art would appreciate that the surface or core of ferritin can be modified to contain molecules that allow it to be detected by optical, radiographic, or magnetic resonance techniques, e.g., radiolabels for positron emission tomography, fluorophores for detection with optical microscopy, or other atoms detected by magnetic resonance imaging. The surface of these modified forms of ferritin can then be cationized as described. For example, the contrast agent can comprise cationized ferritin or cationized modified ferritin. A person skilled in the art would appreciate that the core of apoferritin can be modified to contain a modified mixed or metal oxide core. The surface of the modified apoferritin can then be cationized as described. The modified metal core can be created to alter or enhance detection of the cationic ferritin by magnetic resonance imaging.

In step 104, images of the kidney are acquired with a MRI system, from directly after injection to up to several days after injection. The signal magnitudes and phases of voxels of regions bound with the contrast agent are different from those of regions not bound with the contrast agent. In step 106, the vascular, glomerular, and interstitial microstructure and function capacity of the kidney are determined by imaging the microstructure elucidated by the accumulated cationic ferritin in the glomeruli or surrounding vasculature, nephron, or interstitial space. The function capacity can be determined by the total perfused glomerular surface area, by the total number of functioning glumeruli, by intrarenal distribution of glomerular volumes, or by image texture of the images (e.g., spatial spectra of line profiles of the images). In step 108, a report of the function capacity is generated.

Using the systems and methods as disclosed herein, individual glomeruli in human kidneys can be detected using intravenous injection of cationized ferritin (CF), followed by MRI. With this approach, the apparent number ($aN_{glom}$) and volume ($aV_{glom}$) of each of the glomeruli can be measured in the whole kidney. They are referred to as "apparent" measurements of glomerular number and volumes because those measurements are based on indirect detection of glomeruli by an exogenous agent and on a computer algorithm to measure the sites of agent accumulation. This technique expands the number of glomeruli that can be practically sampled by many orders of magnitude: from hundreds of glomeruli using stereology to all functioning glomeruli in the kidney (of the order of $10^5$-$10^6$ glomeruli). The MRI technique allows direct translation to clinical practice to aid in the evaluation of transplant allografts, the diagnosis of kidney disease, and the quantitation of nephron endowment in children born early or with low birth weight.

The MRI-based measurements of $aN_{glom}$ and $aV_{glom}$ using the systems and methods disclosed herein agree well with the estimates obtained using stereology. Due to the difference in the number of glomeruli sampled using each method and the heterogenous nature of human kidneys, these two measurements may not be in perfect agreement. Furthermore, glomerulus-like dark spots in the control kidney can be due to small regions of residual blood, which can yield ~6% false positive rate.

The systems and methods can mark functioning glomeruli in the kidney. When a patient has significant and uncontrolled hypertension resulting in vascular and glomerular pathology, histopathology reveals that glomeruli and arterioles are severely sclerosed in the regions of the cortex that lacked CF-labeled glomeruli. The glomeruli in these regions may be under-perfused or abnormal. The images acquired with the systems and methods show glomeruli with poor ferritin labeling, sclerotic glomeruli with no open capillaries, and possibly atubular glomeruli or obstruction of collecting ducts; all of them with little, if any, ferritin signal and therefore representing a population of non-functioning glomeruli. To the best of Applicants' knowledge, this is the first time that large regions of non-functioning glomeruli have been detected in an intact human kidney. The systems and methods disclosed herein can also show vascular remodeling and CF accumulation at sites of vascular remodeling. CF tends to accumulate to vasculature undergoing remodeling, which can appear glomerulus-like to the image processing algorithm and in turn cause over counting of glomeruli. Morphology may distinguish CF-related MRI signal changes in glomeruli from those that occur due to vascular changes and blood- and CF-artifact.

The 3D MRI-based technique also enables calculation of the apparent glomerular volume distribution in CF-labeled kidneys. The glomerular volume distributions show a large number of small "glomeruli". From stereological estimates of individual glomerular volumes (IGV) in human kidneys, glomeruli detected by MRI with volumes less than $2.4 \times 10^{-3}$ $mm^3$ are true glomeruli. A remaining ~6% of the small apparent glomeruli may be due to the same systematic artifacts observed in the unlabeled control kidney. There are then two possible sources of the remaining ~14% of apparent glomeruli: spurious labeling of CF in non-glomerular structures or partial CF-labeling in some glomeruli, or both. These erroneous glomeruli can be excluded by setting a strict lower image-processing threshold on the IGV measurements. But, caution may be needed in adjusting this threshold to ensure that IGV is not simply adjusted to give a "correct" result. Nonetheless, the intrarenal distribution of apparent glomerular volumes can be a powerful parameter for assessing glomerular hypertrophy and shrinkage in health and disease.

The spatial distribution of CF accumulation in the kidney can be analyzed by image texture analysis. For example, the CF-related image darkening in a kidney with the least reported nephrosclerosis is punctuate and associated with spatial power spectral peaks between $k=1.2$ and $1.5\ mm^{-1}$. For a kidney with only mild nephrosclerosis, spectral peaks are at both $k=0.8$ and $1.2\ mm^{-1}$. In comparison, in kidneys with profound arteriolosclerosis and nephrosclerosis, the CF-related signal darkening appears diffuse and is associated with a spatial power spectral peak at $k=0.8\ mm^{-1}$—a different spatial frequency than that of a healthier kidney. This diffuse labeling, quantified using the spatial power spectrum, can result from leakage of protein past the glomerular capillary wall into Bowman's space and the proximal tubule. The spectra show populations of healthy ($k=1.2$ mm$^{-1}$) and sclerotic (k=0.8 mm$^{-1}$) glomeruli. Image texture analysis can be used to quantify morphological changes with disease progression.

In one embodiment, CF creates contrast in $T_2$*-weighted MRI by de-phasing the spins of water protons surrounding the site of CF-accumulation. The volume over which this de-phasing is seen in $T_2$*-weighted MRI images depends on the amount of accumulated CF and the image acquisition parameters. Thus, when measuring $aV_{glom}$ with $T_2$*-weighted MRI, imaging parameters are considered and CF-dosage is minimized. While a large CF dose of 300 mg/kg kidney weight can be used, intravenous doses of just 0.6-1 mg/kg body weight of CF are sufficient to visualize rat glomeruli with $T_2$*-weighted MRI and have minimal effects on kidney, liver, and immune function biomarkers. In another configuration, glomeruli can be labeled with a highly sensitive $T_1$-shortening (bright) MRI "paraCF" contrast agents, allowing for improved in vivo detection of glomeruli with $T_1$-weighted MRI. Using $T_1$-shortening contrast agents can eliminate the de-phasing artifacts found in $T_2$*-weighted MRI that might affect volume measurements, and reduce required dosage of the agent by about 100 fold. Such an agent can greatly improve glomerular detection in vivo against the dark blood background and allow for doses that may have a trivial effect on the inherent charge of the GBM.

The ability to clinically measure glomerular morphology and local protein leakage has the potential to directly improve patient care and clinical outcomes. Measurements of glomerular morphology can be used to assess the viability of kidneys from both living and deceased donors, ensuring that a donor kidney has sufficient filtration surface area. Noninvasive glomerular morphological measurements also allows younger recipients to receive kidneys possessing a nephron number sufficient to match their future lifespan. Individuals at risk for CKD can receive an individualized risk assessment using this technique, enabling early detection and regular monitoring of kidney disease. Development of highly-sensitive, $T_1$-shortening (bright) contrast agents and advancements in radio frequency hardware for high resolution in vivo MRI of the kidney have made it possible to visualize glomeruli in vivo in a matter of minutes. Furthermore, initial study of the toxicity and bio-distribution of CF suggest MRI-detectable doses of CF to be minimally toxic. Production of recombinant human ferritin may further reduce toxicity. It is increasingly important to determine the minimum dose of CF needed to detect glomeruli in human studies with MRI. the in vivo detectable limit of intravenous CF in humans may be 0.56 mg/kg.

Kidney diseases are heterogeneous in nature and can cause a wide range of morphological changes to the glomerulus or nephron structure that could be determined with MRI enhanced by cationic contrast agents. These changes can include decreases in the number of functioning glomeruli, potentially detected through a difference in the ratio of glomerular to cortical volume (cortical glomerular density). This is a demonstrated diagnostic marker with histological techniques. They can also includes changes in glomerular permeability, reflected in the distribution of the cationic nanoparticles after injection. Diagnosis of kidney disease on the basis of MRI measurements after labeling with glomerulus-targeted contrast agents may therefore incorporate both image analysis and statistical analysis of the glomerular volume or glomerular number, or the spatial distribution of the glomeruli, or the spatial distribution of the contrast agent in the kidney.

Figure 8:
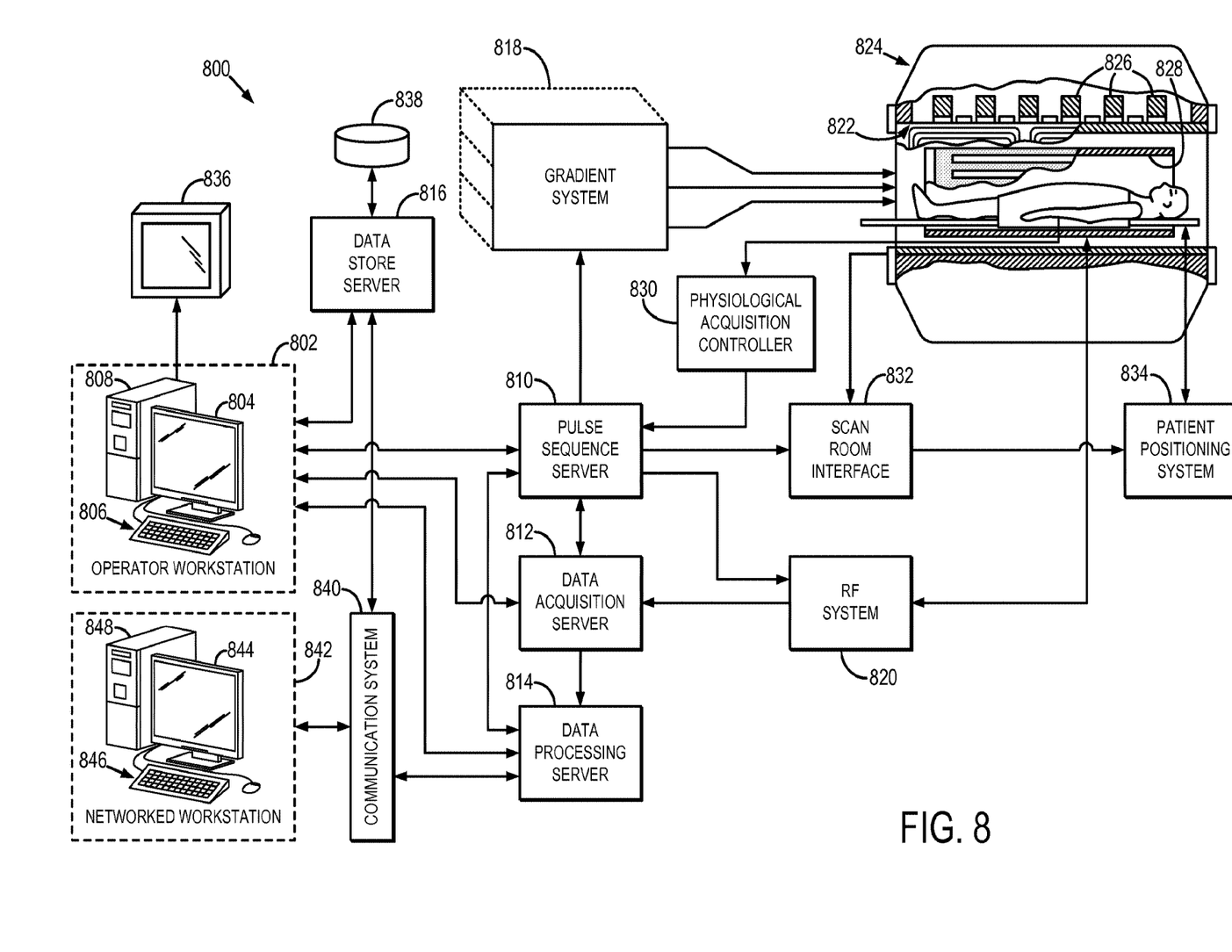
FIG. 8 is a block diagram of an example of a magnetic resonance imaging (MRI) system configured to employ the present disclosure.

The system and method disclosed herein can be used with an MRI system, such as the below-described system 800.

Referring particularly to FIG. 8, an example of a magnetic resonance imaging (MRI) system 800 is illustrated. A clinical (human sized) system is illustrated herein as a non-limiting example. The MRI system can also be a pre-clinical (e.g., rodent-sized) MRI system or a three-axis gradient-equipped nuclear magnetic resonance (NMR) system. The MRI system 800 includes a workstation 802 having a display 804 and a keyboard 806. The workstation 802 includes a processor 808 that is commercially available to run a commercially-available operating system. The workstation 802 provides the operator interface that enables scan prescriptions to be entered into the MRI system 800. The workstation 802 is coupled to four servers: a pulse sequence server 810; a data acquisition server 812; a data processing server 814; and a data store server 816. The workstation 802 and each server 810, 812, 814, and 816 are connected to communicate with each other.

The pulse sequence server 810 functions in response to instructions downloaded from the workstation 802 to operate a gradient system 818 and a radiofrequency (RF) system 820. Gradient waveforms necessary to perform the prescribed scan are produced and applied to the gradient system 818, which excites gradient coils in an assembly 822 to produce the magnetic field gradients $G_x$, $G_y$, and $G_z$ used for position encoding MR signals. The gradient coil assembly 822 forms part of a magnet assembly 824 that includes a polarizing magnet 826 and a whole-body RF coil 828 (or a head (and neck) RF coil for brain imaging).

RF excitation waveforms are applied to the RF coil 828, or a separate local coil, such as a head coil, by the RF system 820 to perform the prescribed magnetic resonance pulse sequence. Responsive MR signals detected by the RF coil 828, or a separate local coil, are received by the RF system 820, amplified, demodulated, filtered, and digitized under direction of commands produced by the pulse sequence server 810. The RF system 820 includes an RF transmitter for producing a wide variety of RF pulses used in MR pulse sequences. The RF transmitter is responsive to the scan prescription and direction from the pulse sequence server 810 to produce RF pulses of the desired frequency, phase, and pulse amplitude waveform. The generated RF pulses may be applied to the whole body RF coil 828 or to one or more local coils or coil arrays.

The RF system 820 also includes one or more RF receiver channels. Each RF receiver channel includes an RF preamplifier that amplifies the MR signal received by the coil 828 to which it is connected, and a detector that detects and digitizes the quadrature components of the received MR signal. The magnitude of the received MR signal may thus be determined at any sampled point by the square root of the sum of the squares of the I and Q components:

$$M=\sqrt{I^2+Q^2} \qquad (1),$$

and the phase of the received MR signal may also be determined:

$$\varphi = \tan^{-1}\left(\frac{Q}{I}\right). \qquad (2)$$

The pulse sequence server 810 also optionally receives subject data from a physiological acquisition controller 830. The controller 830 receives signals from a number of different sensors connected to the subject, such as electrocardiograph (ECG) signals from electrodes, or respiratory signals from a bellows or other respiratory monitoring device. Such signals are typically used by the pulse sequence server 810 to synchronize, or "gate," the performance of the scan with the subject's heart beat or respiration.

The pulse sequence server 810 also connects to a scan room interface circuit 832 that receives signals from various sensors associated with the condition of the subject and the magnet system. It is also through the scan room interface circuit 832 that a subject positioning system 834 receives commands to move the subject to desired positions during the scan.

The digitized MR signal samples produced by the RF system 820 are received by the data acquisition server 812. The data acquisition server 812 operates in response to instructions downloaded from the workstation 802 to receive the real-time MR data and provide buffer storage, such that no data is lost by data overrun. In some scans, the data acquisition server 812 does little more than pass the acquired MR data to the data processor server 814. However, in scans that require information derived from acquired MR data to control the further performance of the scan, the data acquisition server 812 is programmed to produce such information and convey it to the pulse sequence server 810. For example, during prescans, MR data is acquired and used to calibrate the pulse sequence performed by the pulse sequence server 810. Also, navigator signals may be acquired during a scan and used to adjust the operating parameters of the RF system 820 or the gradient system 818, or to control the view order in which k-space is sampled. In all these examples, the data acquisition server 812 acquires MR data and processes it in real-time to produce information that is used to control the scan.

The data processing server 814 receives MR data from the data acquisition server 812 and processes it in accordance with instructions downloaded from the workstation 802. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 814 are conveyed back to the workstation 802 where they are stored. Real-time images are stored in a data base memory cache (not shown), from which they may be output to operator display 804 or a display 836 that is located near the magnet assembly 824 for use by attending physicians. Batch mode images or selected real time images are stored in a host database on disc storage 838. When such images have been reconstructed and transferred to storage, the data processing server 814 notifies the data store server 816 on the workstation 802. The workstation 802 may be used by an operator to archive the images, produce films, or send the images via a network or communication system 840 to other facilities that may include other networked workstations 842.

The communication system 840 and networked workstation 842 may represent any of the variety of local and remote computer systems that may be included within a given clinical or research facility including the system 800 or other, remote location that can communicate with the system 800. In this regard, the networked workstation 842 may be functionally and capably similar or equivalent to the operator workstation 802, despite being located remotely and communicating over the communication system 840. As such, the networked workstation 842 may have a display 844 and a keyboard 846. The networked workstation 842 includes a processor 848 that is commercially available to run a commercially-available operating system. The networked workstation 842 may be able to provide the operator interface that enables scan prescriptions to be entered into the MRI system 800.

The following examples are presented for illustrative purposes only, and are not intended to limit the scope of the present invention in any way.

EXAMPLES

Sample Preparation

Cationized horse spleen ferritin (CF, Molecular weight=475 kD) was synthesized. Four human kidneys were obtained at autopsy through a donor network after Institutional Review Board approval and informed consent. The Organ Procurement Officer deemed the kidneys unsuitable for transplant. A request and informed consent for research was obtained only after the kidneys were deemed unsuitable for transplant. The kidneys were flushed at autopsy with heparinized saline and stored in University of Wisconsin preservation solution and, within 24 hours, the renal artery was catheterized and the kidneys were perfused with 120 ml of phosphate buffered saline (PBS). Three kidneys (hereafter referred to as kidneys CF1, CF2, and CF3) were perfused with 300 mg of CF in PBS per kg by kidney weight (Table 1). The kidneys were then perfused with 120 ml of PBS to remove any unbound CF and then perfused with 10% neutral buffered formalin. One kidney received no CF (as a naive control), but received the same number of PBS and formalin perfusions. A minimum of 3 biopsies (~1 $mm^3$) were taken from random locations in the cortex from each kidney and prepared for immunofluorescence and transmission electron microscopy (detailed below). Targeted biopsies were also taken from the cortex of the CF2 kidney. The reasons for this are discussed below. All kidneys were stored in 10% neutral buffered formalin at 4° C.

TABLE 1

Clinical data, stereological estimates, and MRI-based data
(*MDRD Study Equation was used to calculate GFR.)

| | | CF1 | CF2 | CF3 |
|---|---|---|---|---|
| Age (yrs) | | 68 | 45 | 37 |
| Gender | | M | F | F |
| Race | | C | AA | C |
| Cause of Death | | Cardiac Arrest | Hypertensive Stroke | Cardiac Arrest |
| Initial Creatine (mg/dl) | | 1.6 | 1.1 | 1.9 |
| Initial GFR (ml/min)* | | 43 | 65 | 30 |
| Peak Creatine (mg/dl) | | 2.9 | 2.7 | 6.05 |
| Last Creatine (mg/dl) | | 2.5 | 2.7 | 6.05 |
| Stereology | $N_{glom}$ (x$10^6$) | 1.13 | 0.74 | 1.46 |
| | $V_{glom}$ (x$10^{-3}$ $mm^3$) | 5.01 | 4.68 | 2.82 |
| | Kidney Weight (g) | 167 | 110 | 186 |
| MRI | $aN_{glom}$ (x$10^6$) | 1.27 | 0.92 | 1.52 |
| | Median $aV_{glom}$ (x$10^{-3}$ $mm^3$) | 4.8 | 3.2 | 3.2 |
| | $aV_{glom}$ Skewness | 1.5 | 2.2 | 1.7 |
| % Difference | $N_{glom}$ % | 12 | 25 | 4 |
| | $V_{glom}$ % | 4 | 32 | 13 |

As shown in Table 1, stereological estimates and MRI-based measurements for $N_{glom}$ and $V_{glom}$ follow a similar trend, though differences between the two techniques are apparent. Due to the difference in the number of glomeruli sampled using each method and the heterogeneous nature of human kidneys, these two measurements may not be in perfect agreement.

Prior to imaging, the CF-labeled and un-labeled control kidneys were removed from formalin and washed three times in 500 ml PBS (for a total of 1.5 L of PBS) over 24 hours. The kidneys were first imaged using a 7T/35 MRI scanner and a 72-mm quadrature transmit/receive radio frequency coil. The whole kidneys were imaged in PBS in a sealed plastic container to keep the tissue hydrated. A $T_2^*$-weighted (TE/TR=20/39 ms) three-dimensional gradient echo fast low angle shot (FLASH) sequence was used to image the entire kidney. MR images were acquired with 3D acquisition using a 117×117×117 µm³ resolution (field of view=6×6×10.5 cm³, matrix size=512×512×896, 5 averages, total scan time=10 hr 39 min per kidney).

After 7T MRI, immunofluorescence and electron microscopy (see below), kidneys were imaged using a 3T MRI scanner and a 32-channel transmit/receive radio frequency head coil. Whole kidneys were imaged in PBS in a sealed plastic container. A $T_2^*$-weighted (TE/TR=20/32 ms) three-dimensional gradient recalled echo (GRE) sequence was used to image the kidney. MR images were acquired with a resolution of 270×270×540 µm³ (Field of view=12×4.9×7.8 cm, matrix size=448×182×144, scan time=4.2 hr in the CF labeled kidney; FOV=12×5.4×6.9 cm, matrix size=448× 200×128, scan time=4 hours in the unlabeled control kidney). A $T_2$-weighted (TE/TR=83/2000 ms, FA=150, matrix size=320×120×51, spatial resolution=400×400×130 µm³, 24 averages, total scan time=41.6 min) Half Fourier Acquisition Single Shot Turbo Spin Echo (HASTE) pulse sequence was also used to acquire an image of the entire control kidney to distinguish cortex and medulla. The CF-labeled kidneys did not require HASTE imaging to distinguish cortex from medulla. One slice was selected from the 3D reconstructed image data and corrected for inhomogeneities by subtracting a low pass filtered version of the image (50×50 Gaussian kernel with s.d.=20 voxels). The slice image intensities were normalized to a range of 0-1 and the cortex and medulla were manually segmented (directly from the $T_2^*$-weighted GRE for the CF-labeled kidney and from the co-registered HASTE $T_2$-weighted image for the naive control). The $T_2$-weighted HASTE image was linearly registered to the gradient echo image using FSL FLIRT).

Transmission Electron Microscopy

Approximately 1 mm³ pieces of tissue were collected from the cortex of each kidney after perfusion of formalin and immediately placed in 2% glutaraldehyde/0.1 M cacodylate solution for overnight fixation. Samples were dehydrated in graded ethanol solutions ranging from 70% to 100%, then infiltrated with and embedded in epoxy resin. The resulting blocks were cut into 70 nm sections and stained with 0.2% osmium tetroxide. Osmium tetroxide precipitates were digested with 1% periodic acid for 12 min. A Philips CM12 transmission electron microscope was used to collect images at 53 kX magnification with an accelerating voltage of 80 kV.

Immunofluorescence

Frozen Tissue

Immunofluorescence (IF) microscopy can be used to confirm labeling of the GBM with CF. Because CF is a protein it is readily detected with IF. Several ~1 mm³ tissue samples were taken from each kidney after perfusion. The biopsies were placed in 10% neutral buffered formalin for 4 hours and stored in PBS overnight. The samples were cryoprotected in 15% sucrose followed by 30% sucrose, then rapidly frozen to −80° C. and cut into 35 µm sections. The sections were washed in PBS, permeabilized with 0.5% Triton X-100, incubated in rabbit anti-horse spleen ferritin, immunostained with an Alexa594 goat anti-rabbit secondary antibody and 4',6-diamidino-2-phenylindole, and imaged on a Zeiss 710 laser scanning confocal microscope.

Formalin-Fixed Tissue

A second round of IF was performed in formalin-fixed tissue after MRI and stereological analysis. Two approaches were used for tissue sampling and paraffin embedding: 1) targeted sampling and 2) random sampling. Targeted sampling, (based on MRI), was used for analysis of the CF2 kidney in order to extract 2 mm³ samples from areas of cortex with good ferritin labeling and areas of cortex with poor ferritin labeling. For CF1 and CF3, similar size blocks were randomly cut from the cortex of the formalin fixed tissue. All formalin-fixed tissue samples were embedded in paraffin. 3 serial sections (4 µm thick each) were cut from each block. The first section was used for IF while the second section was used for PAS staining. For IF, following sectioning, sections were rehydrated in 100% ethanol (5 min), 70% ethanol (5 min) and then phosphate buffered saline (PBS; 5 min). Sections were then subjected to an antigen retrieval step, which involved immersion in Target Retrieval Solution (DAKO, S1699) for 20 min at a controlled temperature of 90.0 in a DAKO PT Link PT10126 system. After cooling, slides were washed in Buffer (DAKO, K8007) and then in 1% filtered Bovine Serum Albumin (BSA) in PBS for 1 h. Sections were then immunostained using an antibody against Wilms' Tumor-1 (WT1) antigen (monoclonal mouse anti-human WT1-DAKO, M356101, clone 6F-H2) a well known podocyte marker that allowed us to confirm glomerular localization and the same rabbit anti-horse spleen ferritin (Sigma-Aldrich), as previously described. After 1 hour incubation at room temperature, sections were labeled with goat anti-mouse Alexa488 (1:2000; Invitrogen A-11008) and goat anti-rabbit Alexa555 (1:1000; Invitrogen A-11001) for another hour at room temperature under light protection. Finally, Prolong Gold with DAPI (Invitrogen P-36931; anti-fade mounting medium) was used for permanent coverslipping and left for 24 h. Confocal images were taken on a Leica SP5 laser confocal microscope. Images were obtained using a 40× objective lens (1.25 NA), using sequential imaging for 488 nm, 555 nm and UV light.

Histopathology and Stereology

The MRI-based measurements of $N_{glom}$ and $V_{glom}$ were validated (after MRI) using a physical disector/fractionator design-based stereological method. In brief, kidneys were weighed and a series of sampling and subsampling steps were applied to select a systematic uniform random sample of 10-15 tissue blocks from the cortex. These blocks were embedded in glycolmethacrylate, serially sectioned at 20 µm and every $10^{th}$ and $11^{th}$ section pair was collected and stained with PAS. The section pairs were viewed with a pair of light microscopes modified for projection. Glomeruli present in one section (the reference section) but not in the paired section (look-up section) were counted according to the disector principle. At the same time glomeruli were counted with the disector principle, stereological grid points overlying glomeruli were counted and used to estimate $V_{glom}$.

A specialist renal pathologist assessed PAS stained glycolmethacrylate sections. Sections from approximately 10 blocks per kidney were examined. 72, 61, and 66 glomeruli were assessed in kidneys CF1, CF2, and CF3, respectively.

Image Processing $N_{glom}$ and the individual volumes of all glomeruli were calculated from the MR images. First, a Hessian for each voxel of the raw MRI volume (in 3D) was used to flag candidate glomerular regions and discern glomeruli in close proximity to each other. This step populated candidate regions and, as a result, dramatically reduced the data size. Five features, including average intensity, divergence, region volumes, shape index, and the Laplacian of Gaussian were extracted in order to remove false positive glomeruli. With those features, a Gaussian Mixture Model clustering algorithm was used to group candidate regions (black dots) into several clusters throughout the volume. Next, all clusters were overlain individually onto the original MRI volume, and clusters that did not identify populations of glomeruli were identified manually and eliminated from further analyses. The remaining black dots were counted as glomeruli and their sizes were measured based on the number of voxels comprising each dot. Clusters of black dots in the control kidney of similar locations and appearance to those of CF-labeled kidneys were counted as false glomeruli to quantify the negative contribution of blood artifact.

To validate the automated algorithm, the number of labeled glomeruli in six 35 mm² sections of the original magnitude MRI volume were counted by eye. The same 35 mm² sections were then compared to the glomeruli in the same images identified by the algorithm. These glomerular counts were compared using a paired Student's two-tailed t-test and were not statistically different ($p > 0.05$) and were well correlated ($R^2 = 0.88$).

Image Texture Analysis

Image texture analysis can be used to assess the pattern of glomerular labeling in the MR images of CF-labeled kidneys. 16 lines (each 64 voxels in length) were drawn through the cortex of each kidney in 7T MRI volumes (all of which have the same FOV and matrix size) and plotted the signal line profile. The location of each line profile was randomly chosen and each profile was oriented through glomeruli that appeared to originate from the same interlobular artery. The spatial power spectrum from each line profile was calculated using Fourier Transform. Spatial power spectra of CF-perfused and control kidneys were compared at each spatial frequency using Student's two tailed t-tests ($\alpha = 0.05$).

Statistics

Statistical analyses were calculated as either two-sample or paired two-tailed Student's t-tests to test the hypothesis that the mean difference between groups is zero ($\alpha = 0.05$).

Results

To investigate the use of CF as a glomerulus-specific MRI contrast agent in humans, CF was injected into the renal artery of three viable (but un-transplantable) human donor kidneys within 24 hours of resection. Saline was injected into one kidney instead of CF as a control. The CF-labeled kidneys are hereafter referred to as kidney CF1, CF2, and CF3. Donor data were investigated to establish possible reasons for any variability in nephron number and CF accumulation in the kidneys measured by MRI (see Histopathology section). These data are shown in Table 1. Notably, the donor of kidney CF2 suffered from severe, untreated hypertension, and the donor of kidney CF1 suffered from mild, treated hypertension.

Referring to FIG. 3, a healthy, CF-inoculated kidney (CF3) (A) and a naive control kidney (C) were imaged at 3T using $T_2^*$-weighted and $T_2$-weighted MRI. While individual glomeruli are not visible in these images due to the lower resolution used to collect the images, the labeling of glomeruli in the CF3 kidney is evident when histograms of $T_2^*$-weighted signal magnitude in the cortex are compared to those of the medulla. A broad (~20%) downward shift in the cortical $T_2^*$-weighted signal magnitude with respect to the medulla is observed in the CF3 kidney (B), while minimal (~2%) differences in cortical and medullary signals are seen in the naive control kidney (D). Regions of interest for the $T_2^*$-weighted control images were defined using half-Fourier acquisition single-shot turbo spin echo (HASTE–$T_2$-weighted) MRI volumes, which provided better contrast between the cortex and the medulla. Shown are examples of the cortical (E) and medullary (F) regions of interest defined from the HASTE MRI volume of the naive control kidney. In addition to separating the cortex from medulla, these ROIs eliminate large blood vessels, calyxes, and the pelvis from the analysis.

Figure 4A:
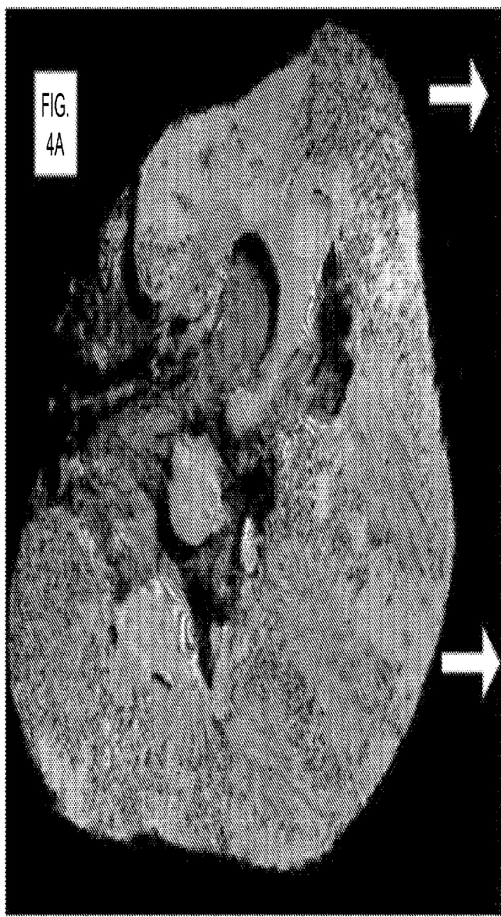
FIG. 4A shows a 7T CF-labeled MR image of a kidney from a patient with untreated hypertension (CF2).
Figure 4B:
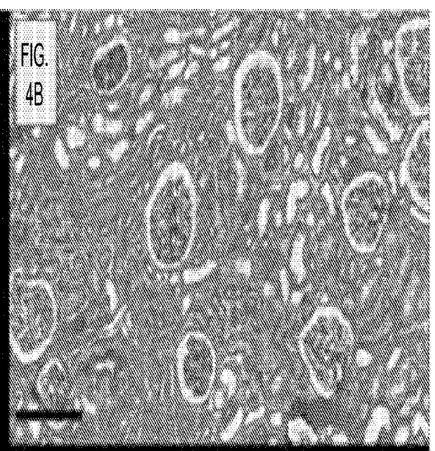
FIG. 4B shows histopathology performed on the cortical regions of the kidney marked by the top arrow in FIG. 4A.
Figure 4C:
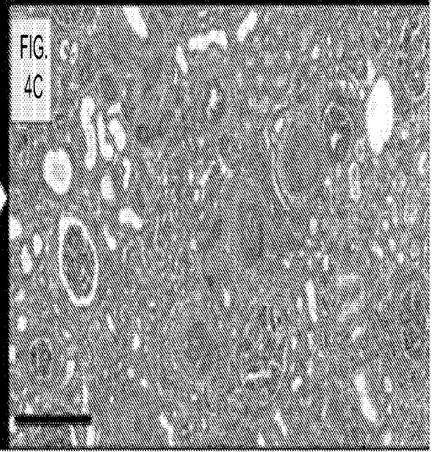

Referring to FIG. 4, 7T MR image of a kidney from a patient with untreated hypertension (CF2) revealed large regions of cortex lacking CF-labeled glomeruli (A). Histopathology performed on the cortical regions that lacked CF-related signal darkening revealed severe sclerosis of glomeruli and arterioles (C), which likely prevented perfusion of glomeruli in these regions. The regions of the CF2 cortex which did have CF-labeled glomeruli showed mild sclerosis. These glomeruli and arterioles appeared substantially healthier than those located in regions that lacked CF-related contrast (B). Scale bars=400 μm.

Figure 5:
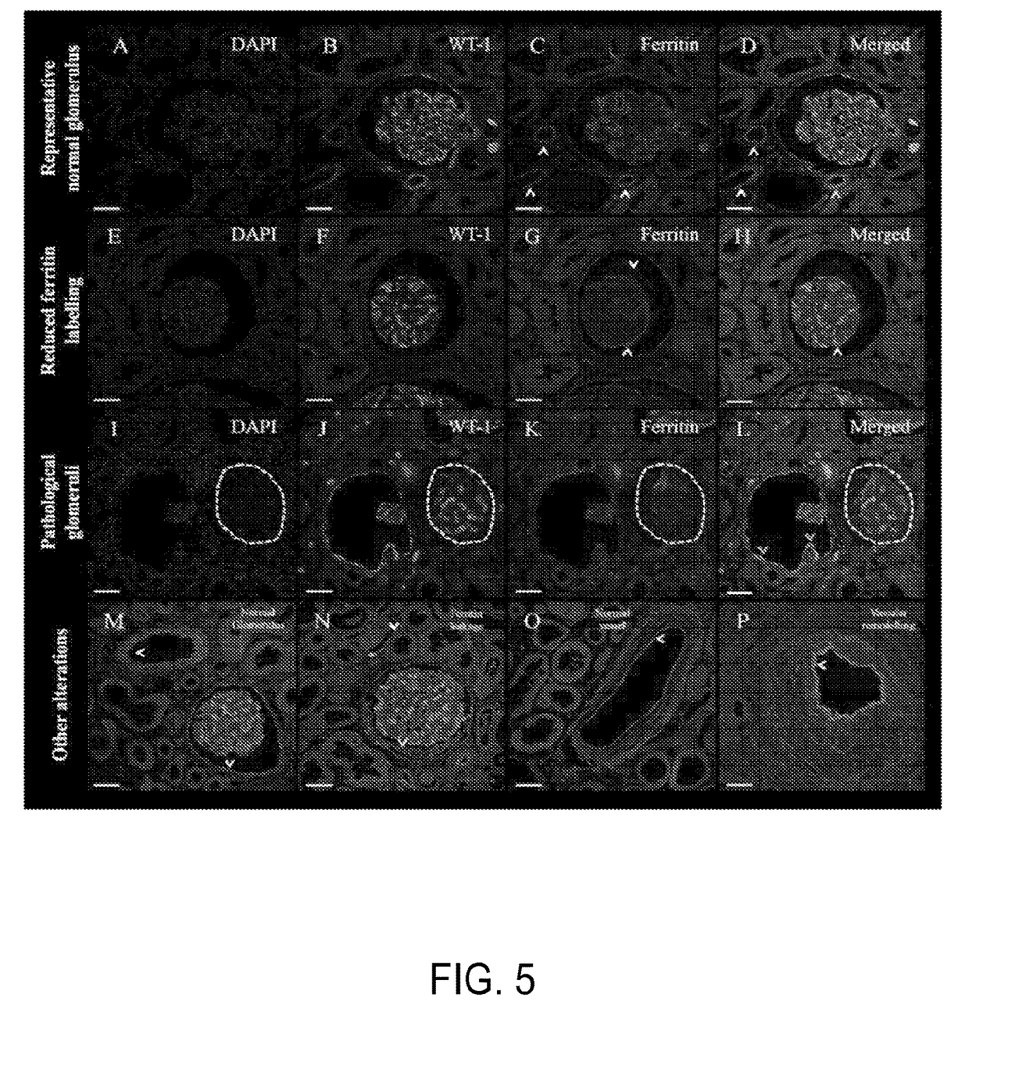

Referring to FIG. 5, immunofluorescence of intravenous CF labeling and histopathology in human donor kidneys is shown. Triple immunofluorescence with an antibody against Wilms Tumor 1 antigen (WT-1) as a marker of healthy mature podocytes (green), ferritin as a marker of injected CF (red) and DAPI as a nuclear marker (blue). A-D shows a normal glomerulus from patient CF3 with strong podocyte labeling and strong ferritin labeling on the GBM and fine ferritin labeling in peritubular capillaries and Bowman's capsule. E-H shows a glomerulus with reduced ferritin labeling in the tuft, and ferritin signal on Bowman's space (very frequent in CF2, regular in CF1 and very rare in CF3). I-L shows two pathological glomeruli. On the left, a glomerulus with expanded Bowman's space, collapsed tuft and WT-1 positive cells on Bowman's capsule: all three features are suggesting an atubular glomerulus or obstructed collecting ducts. On the right (dashed ellipsis), a collapsed glomerular tuft without open capillaries and indirect signs of glomerulosclerosis. M shows a normal glomerulus (present in all subjects; very frequent in CF3). N shows a glomerulus with ferritin "leakage" into the Bowman's space (frequent finding in CF1 and CF2). O shows a normal vessel (frequent finding in CF3). P shows a vessel with vascular remodeling (very common in CF2, and sporadic finding in CF1). White arrowheads (e.g., those in FIG. 5, C, D, G, H, M, N, O, and P) represent ferritin labeling outside the glomerular tuft, green arrowheads (e.g., those in FIG. 5, L) show WT-1 expression in cells on Bowman's capsule. Scale bars=50 μm.

Figure 6:
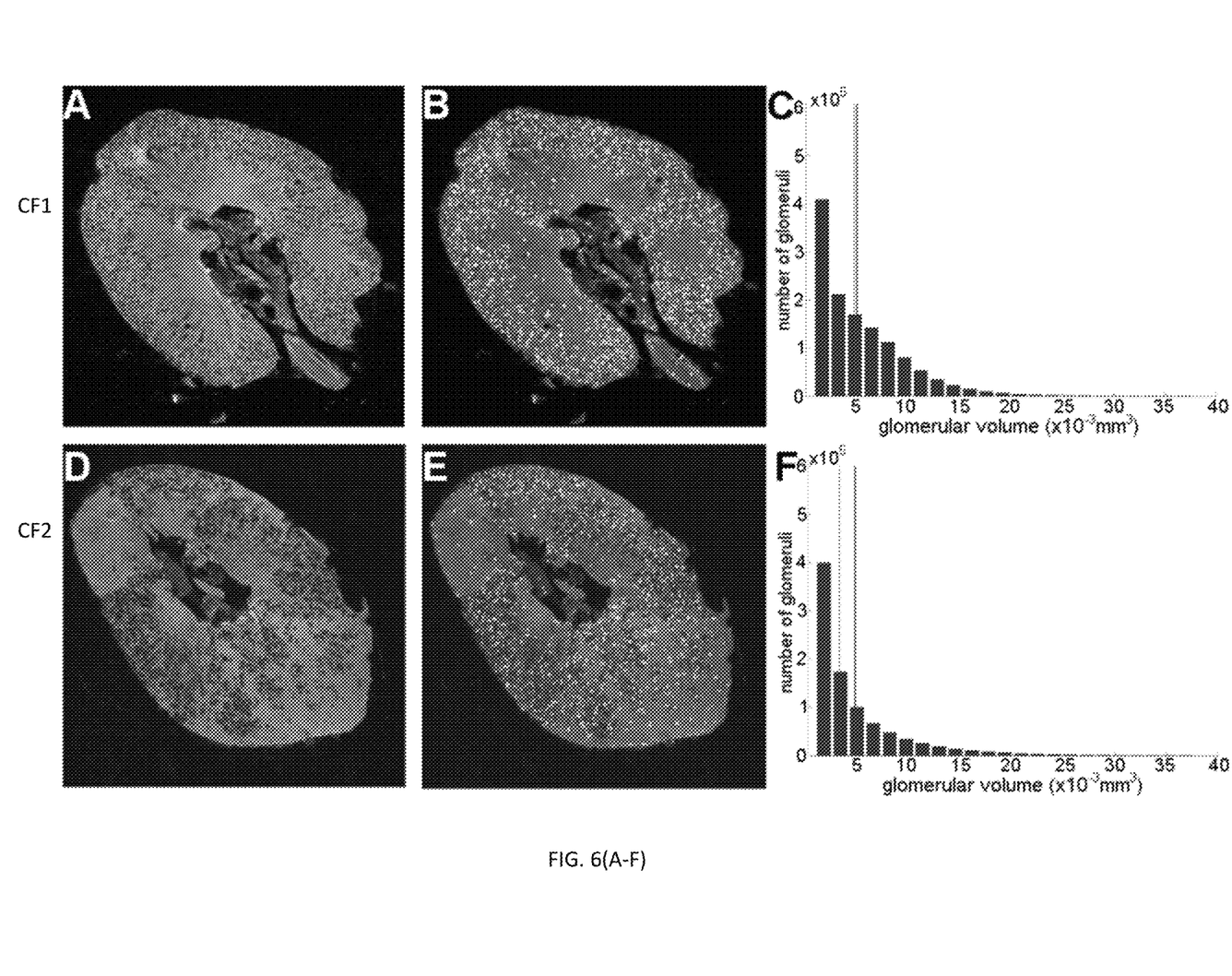

Referring to FIG. 6, glomeruli are made visible in all three CF-labeled kidneys (A, D, G) and the glomerular segmentation algorithm was able to identify, count, and measure the volume of labeled glomeruli (B, E, H). Identified glomeruli are assigned an arbitrary color for visualization purposes in these panels. The majority of regions defined as glomeruli by the algorithm exist in the cortical and juxtamedullary regions of the representative slice. The control kidney (J, K) shows very few regions defined as 'glomeruli'—most of which are likely attributed to residual blood. The MRI-measured apparent glomerular volume ($aV_{glom}$) distribution for each kidney is shown, along with a grey line showing the median MRI-measured $aV_{glom}$ and a black line showing the $V_{glom}$ estimate obtained using stereology (C, F, I, and L). Note that no stereological measurement is available for the control kidney.

Figure 7:
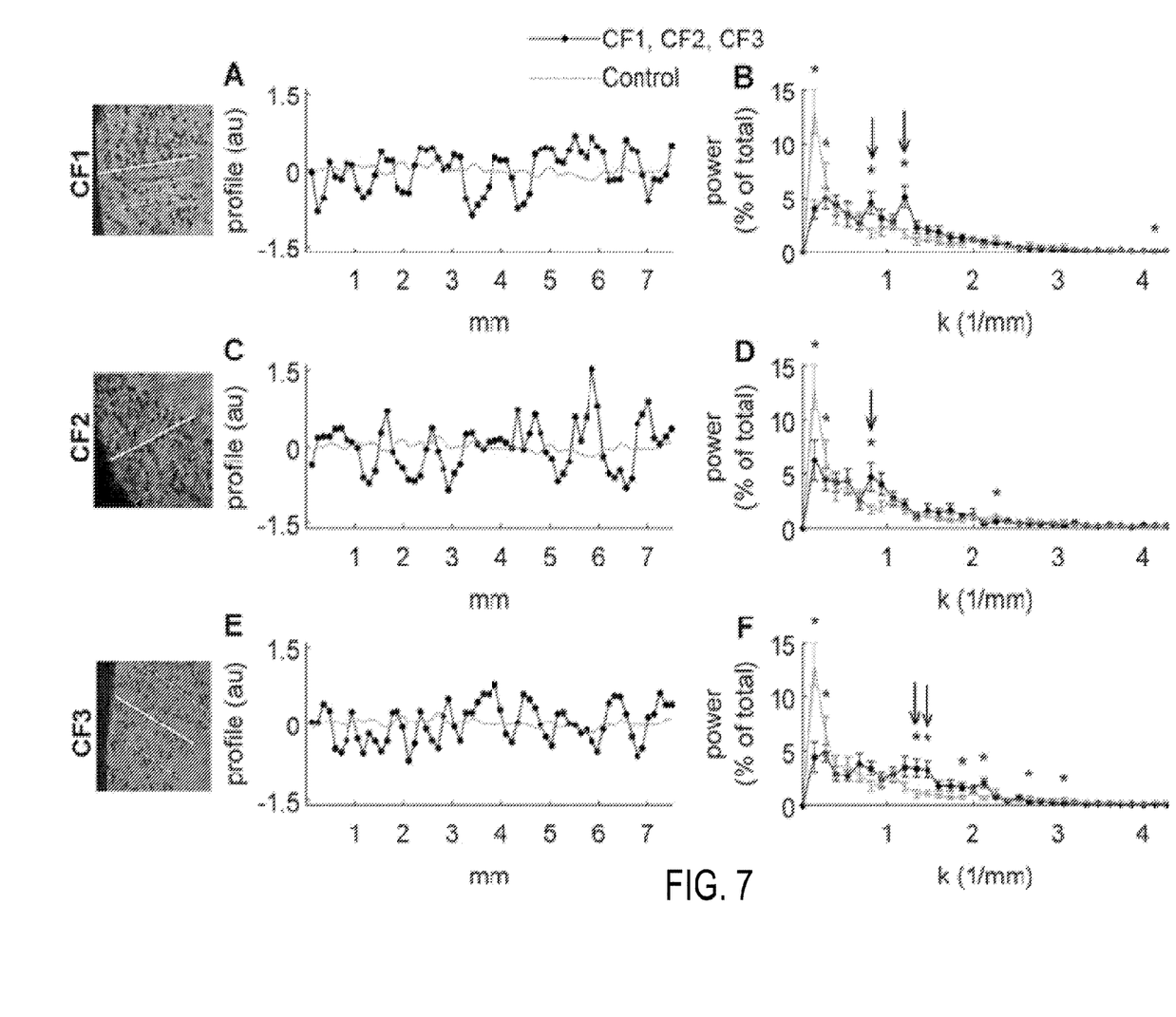

Referring to FIG. 7, line profiles (16 per kidney) were drawn through the cortex of each CF-labeled kidney in 7T MRI volumes (all of which have the same field of view (FOV) and matrix size). Here the line signal profiles of the solid white profiles are plotted (A, C, and E) and the mean power spectrum for the 16 line profiles are shown (B, D, and F). Black traces are data from CF-labeled kidneys and grey traces are data from the naive control. Arrows point to spatial spectral peaks of particular interest. Qualitatively, the line profiles for the CF-labeled kidneys appear different from one another, with the CF3 line profiles being mostly composed of relatively high frequency oscillations, the CF2 oscillations being mostly composed of relatively low frequency oscillations, and the CF1 kidney being composed of a mixture of high and low frequency components. The line profile signal changes associated with the appearance and disappearance of sites of CF accumulation in the CF1 kidney correspond to two spectral peaks; one at $k=0.8$ mm$^{-1}$ (4.5% of total signal) and one at $k=1.2$ mm$^{-1}$ (5% of total signal) (B). The line profile signal changes associated with CF accumulation in the CF2 kidney correspond to only a low frequency spatial signal oscillation at $k=0.8$ mm$^{-1}$ and account for 5% of the total signal along the line profiles (D). The line profile signal changes associated with the accumulation of CF in the CF3 kidney correspond only to high frequency spatial oscillations between $k=1.2$ and $1.5$ mm$^{-1}$ which account for 10% of the total signal along the line profiles (F). Histopathology showed that CF2 had substantial nephrosclerosis, CF1 had mild nephrosclerosis, and CF3 had minimal nephrosclerosis; therefore the prominence of low frequency spectral peaks may suggest the advancement of nephrosclerosis. Stars represent a statistically significant difference between the CF-labeled kidney and the naive control ($p<0.04$) and arrows denote peaks of particular interest. Error bars represent mean±one standard deviation between power spectra of sixteen randomly chosen line profiles.

MRI

Figure 2A:
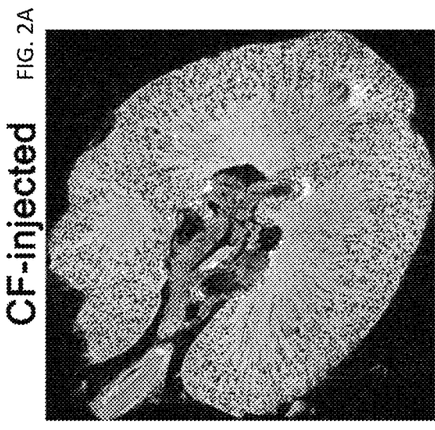
FIG. 2A shows an magnetic resonance (MR) image of a CF-labeled human kidney.
Figure 2B:
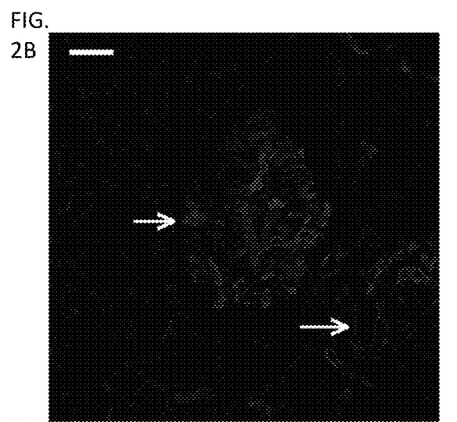
FIG. 2B shows immunofluorescence of the CF-labeled human kidney in FIG. 2A.
Figure 2C:
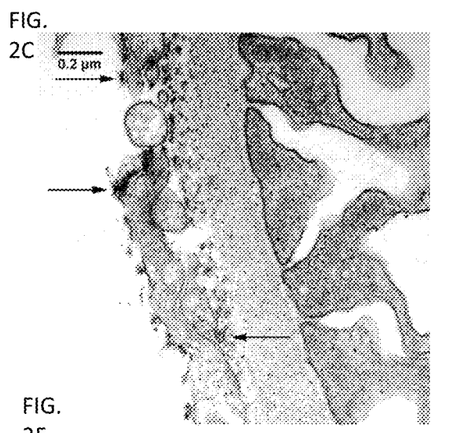
FIG. 2C shows the transmission electron microscopy of the CF-labeled kidney in FIG. 2A.
Figure 2D:
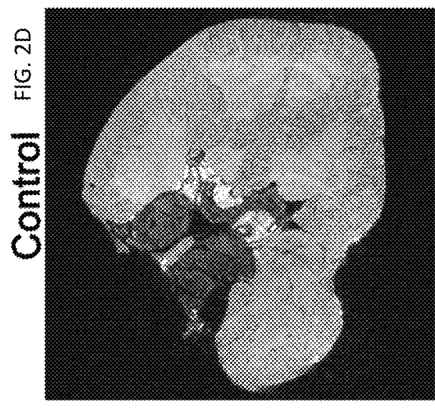
FIG. 2D shows an MR image of a naive control kidney.
Figure 2E:
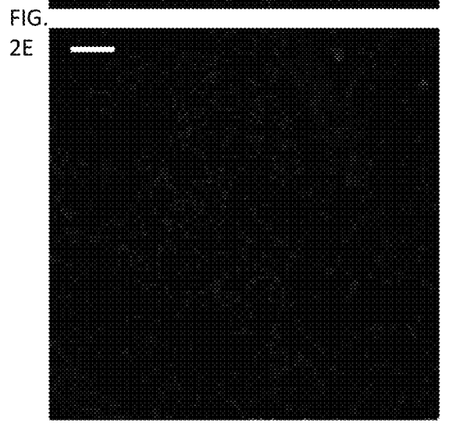
FIG. 2E shows immunofluorescence of the naive control kidney in FIG. 2D.
Figure 2F:
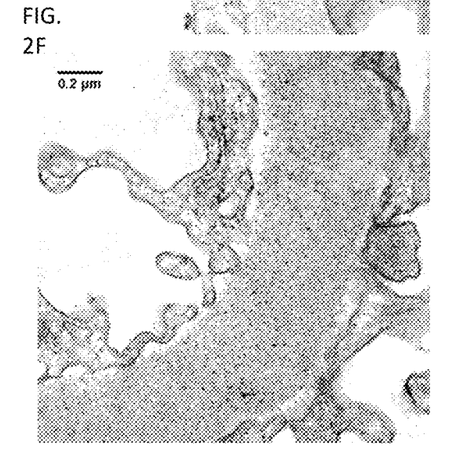
Figure 3A:
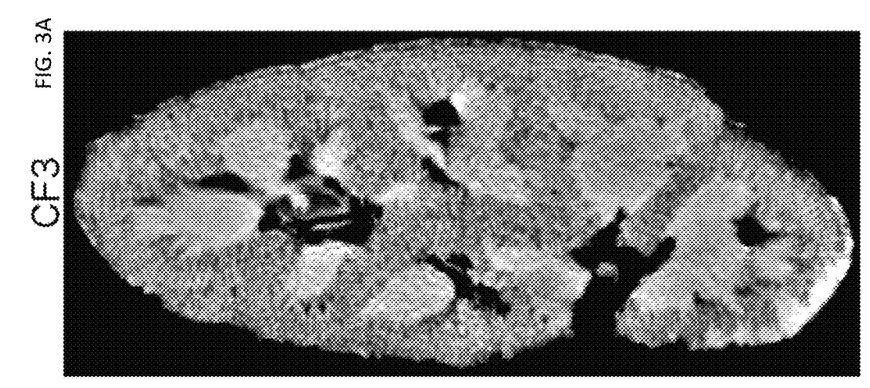
FIG. 3A shows an MR image of a healthy, CF-inoculated kidney (CF3) at 3T using $T_2^*$-weighted and $T_2$-weighted MRI.
Figure 3B:
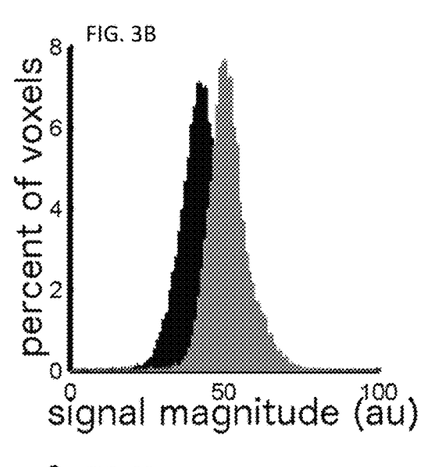
FIG. 3B shows plots of the signal magnitudes of cortex and medulla using the image in FIG. 3A.
Figure 3C:
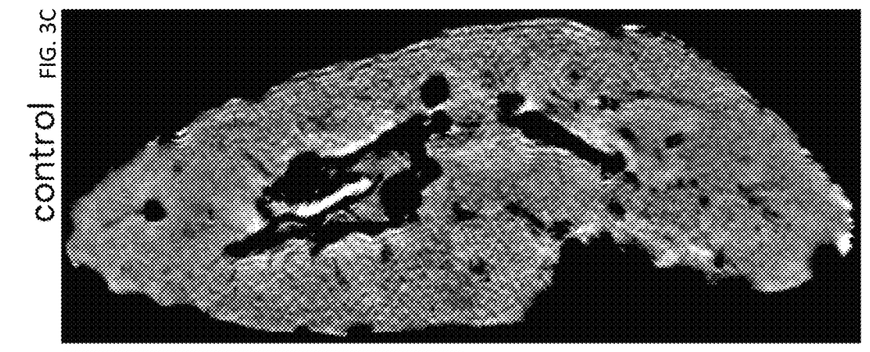
FIG. 3C shows an MR image of a naive control kidney at 3T using $T_2^*$-weighted and $T_2$-weighted MRI.
Figure 3D:
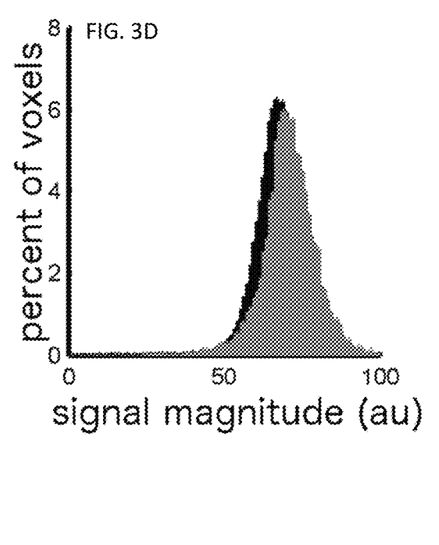
FIG. 3D shows plots of the signal magnitudes of cortex and medulla using the image in FIG. 3C.
Figure 3E:
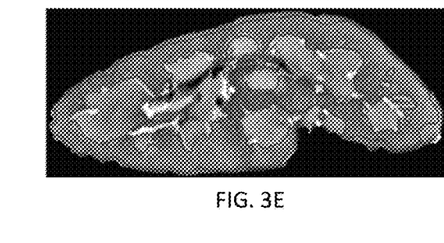
FIG. 3E shows an example cortical regions of interest defined using half-Fourier acquisition single-shot turbo spin echo (HASTE–$T_2$-weighted) MRI of the naive control kidney in FIG. 3C.
Figure 3F:
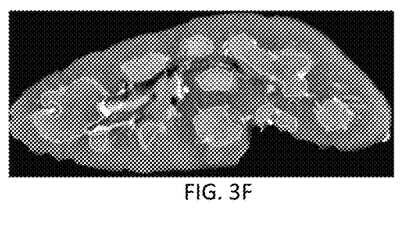
FIG. 3F shows an example medulla regions of interest defined using HASTE MRI of the naive control kidney in FIG. 3C.

The intact, fixed donor kidneys were imaged on a 7T MRI scanner using a 3D gradient-recalled echo pulse sequence. Referring to FIG. 2, intravenously injected CF specifically labels glomeruli in perfused human donor kidneys, making them visible with 7T MRI. MRI of CF-labeled human kidneys reveals punctuate dark spots throughout the cortex (A). A naive control kidney showed no such spots but did show minimal signal loss caused by residual blood (D). Immunofluorescence confirmed the accumulation of CF (red) in glomeruli (B, top arrow) and leakage of CF into tubules of CF-perfused kidneys (B, bottom arrow). Naive control glomeruli remained clear of CF-related immunofluorescence (E). Transmission electron microscopy confirmed the accumulation of CF in the glomerular basement membrane (GBM) and endothelial glycocalyx (arrows) (C). The glomerular capillary walls of the naive control kidney were clear of any punctate TEM signal darkening associated with the accumulation of CF (F). As shown in FIG. 2A, the MR images exhibited dark spots throughout the renal cortex of the CF-labeled kidneys. Each dark spot in the cortex is ~50-80% darker than the surrounding cortex. These dark spots were not present in the un-labeled control kidney (FIG. 2D). The punctate darkening of each glomerulus was caused by the accumulation of the superparamagnetic CF in the GBM. The labeled glomeruli defined the boundary between the cortex and medulla and revealed the individual lobes and papillae of the kidney. The specific binding of CF to the glomerulus was confirmed with immunofluorescence microscopy (IF) (FIGS. 2, B and E). Transmission electron microscopy showed CF bound to the GBM as well as to the glycocalyx of glomerular endothelial cells (FIG. 2C). TEM did not reveal this staining in control kidneys (FIG. 2F).

To assess the possibility of detecting glomeruli in typical clinical MRI systems, CF-labeled kidneys were also scanned at lower resolution on a clinical 3T MRI scanner (FIG. 3). While individual glomeruli were not visible at this lower resolution, the average image magnitude in the cortex of CF-labeled kidneys was ~20% lower than in the medulla. Minimal difference between image magnitude in the cortex and medulla (<2%) was seen in the un-labeled control kidney. Thus, CF labeling can be detected with typical clinical MRI systems by measuring the ratio of cortical to medullary image intensity.

Leakage of CF through the GBM into the proximal tubule was visible in MRI and IF images of kidneys CF1 and CF2 (FIG. 4A, FIG. 5G, FIGS. 6, A and D, and zoomed MRI panels of FIG. 7). The leakage of CF past the glomerular capillary wall appeared as diffuse CF accumulation and MRI signal darkening, similar to leakage previously observed in a rat model of focal and segmental glomerulosclerosis. CF was visible by IF in the tubules (FIG. 2B, bottom arrow) and Bowman's capsules (FIG. 5N) of kidney CF1, consistent with CF leakage in kidneys CF1 and CF2. Based on MRI, large regions of the cortex of kidney CF2 lacked CF-labeled glomeruli (FIG. 4A) and IF (FIG. 5, E-H). Histopathological examination of this kidney, (described below), suggested that this was due to severe glomerular and arteriolar sclerosis that prevented perfusion of those areas of the cortex (FIG. 4). In comparison, the MR image darkening in glomeruli of kidney CF3, (histopathologically deemed the healthiest of the group), was punctate and appeared throughout the entire cortex of the kidney (see FIG. 6G), suggesting minimal protein leakage and vascular damage. This was supported by IF (FIG. 5, A-D).

Immunofluourescence

IF analysis with a double labeling for ferritin and WT-1 revealed that the CF1 kidney exhibited a large number of apparently healthy glomeruli, with moderate leakage of CF into Bowman's capsule. The CF2 kidney contained a large number of poorly labeled glomeruli (FIG. 5, E-H). CF2 also contained a large number of glomeruli with an expanded Bowman's space, collapsed glomerular tufts, and WT-1 positive cells—all features compatible with atubular glomeruli or obstructed collecting ducts (FIG. 5, I-L). There was heavy leakage of CF into Bowman's space and signs of vascular remodeling or thickening of the vessel wall (FIG. 5N). Signs of vascular remodeling (FIG. 5P) were particularly apparent in the regions of the CF2 kidney that lacked CF-related MRI signal changes. Interestingly, remodeling vessels appeared to accumulate a large amount of CF in this kidney, suggesting highly charged endothelial surfaces. The CF3 kidney was dominated by healthy glomeruli, with a large accumulation of CF in the glomerular basement membrane and light accumulation of CF in the peritubular capillaries and Bowman's capsules (FIG. 5, A-D).

Histopathology

Histopathology of kidney CF1 revealed four sclerotic glomeruli of the 72 examined. There was widespread patchy fibrosis and tubular dilation and atrophy with mild diffuse lymphohistiocytic leukocytic infiltration within the interstitium. The arteries were sclerotic with variable hyalinosis. Overall there was minor nephrosclerosis and acute tubular injury.

Five totally sclerosed glomeruli of the 61 examined and one with perihilar segmental sclerosis in kidney CF2. In the regions of CF-labeled tissue (FIG. 4B), the interstitium had widespread mild, patchy fibrosis, tubules were mildly dilated and atrophic, and a moderate lymphohistiocytic infiltrate was present that included eosinophils. The arterioles were tortuous and showed marked hyalinosis with intimal sclerosis. Within the unlabeled regions of CF2, the degree and number of severely sclerotic glomeruli was striking (FIG. 4C). Vascular involvement was evident, with both the arteries and arterioles severely thickened. In some unlabeled areas, it was impossible to distinguish sclerotic glomeruli from obstructed arterioles. The tubules in the unlabeled areas were unaffected overall, but did occasionally contain cast material. We concluded that the observed lack of CF-labeled glomeruli in some regions of kidney CF2 was correlated with focal sclerosis and vascular damage at those locations.

Kidney CF3 had one sclerotic glomerulus of the 66 glomeruli examined, with no mesangial proliferation or segmental sclerosis within the glomeruli. The interstitium showed slight fibrosis and tubular atrophy with minimal lymphohistiocytic interstitial inflammatory infiltrate. The arteries were either normal or had mild sclerosis of the intima. The tubules were mildly dilated with scattered uromodulin casts. There were only very mild changes of acute tubular injury and very mild background nephrosclerosis.

Quantitative Morphology

Custom software is used to measure glomerular number and individual glomerular volume from the MR images. The custom 3D image processing software identified (FIG. 6, B, E, H, and K) and measured the volume of labeled glomeruli (FIG. 6, C, F, I, and L) in the MRI volumes of CF-labeled kidneys.

The number of glomeruli identified in the MR images by the software yielded the total apparent number of glomeruli per kidney ($aN_{glom}$). These data were compared to stereological estimates of $N_{glom}$ (Table 1). Both MRI- and stereology-based measurements were consistent with the range of $N_{glom}$ reported in the literature. The algorithm counted $0.057 \times 10^6$ false glomeruli in the one naive control kidney, yielding a false-positive rate of the image processing program of ~6%.

Using the same software, we estimated the median apparent glomerular volumes ($aV_{glom}$) using the MR images and compared them to stereological estimates (Table 1). These median volumes are consistent with those reported in the literature. The MRI-based measurements were used to generate the glomerular volume distribution for each CF-labeled kidney, which cannot be obtained with other techniques (FIG. 6, C, F, I, and L). We observed a large number of glomeruli in these distributions with volumes of $2.4 \times 10^{-3}$ mm$^3$ or less. This was unexpected, because prior stereological estimates of glomerular volumes in human kidneys suggest that only ~10% of the total number of glomeruli in a kidney should have volumes this small (data not shown). In MRI, these glomeruli represented ~30% of the total number of glomeruli.

Image Texture Analysis

To detect morphological differences between MRI volumes of CF-labeled donor kidneys (FIG. 7), image texture analysis were performed. This analysis included spatial power spectra associated with line profiles randomly drawn in the cortex in the MR images. The line signal profiles in the CF1 kidney, which showed only mild nephrosclerosis, were composed of a mix of high and low frequency oscillations with CF-related spatial spectral peaks at $k=0.8$ mm$^{-1}$ (4.5% of total signal power) and $k=1.2$ mm$^{-1}$ (5% of total signal power). The line signal profiles in kidney CF2, histopathologically assessed as the least healthy kidney of the group, were composed of low frequency CF-related oscillations corresponding to a CF-related spatial spectral peak at $k=0.8$ mm$^{-1}$ which accounted for 5% of the total signal power along the line profiles. The line signal profiles in CF3, defined by histopathology as the healthiest kidney of the group, demonstrated high spatial frequency oscillations between $k=1.2$ and $1.5$ mm$^{-1}$ and account for 10% of the total signal power along the line profiles.

The present invention has been described in terms of one or more preferred embodiments, and it should be appreciated that many equivalents, alternatives, variations, and modifications, aside from those expressly stated, are possible and within the scope of the invention.

As used in the claims, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The invention claimed is:

1. A magnetic resonance imaging (MRI) system, comprising:
    a magnet system configured to generate a polarizing magnetic field about at least a portion of a subject arranged in the MRI system, wherein the subject comprises a human kidney preserved for transplant;
    a magnetic gradient system including a plurality of magnetic gradient coils configured to apply at least one magnetic gradient field to the polarizing magnetic field;
    a radio frequency (RF) system configured to apply an RF field to the subject and to receive magnetic resonance (MR) signals therefrom;
    a computer system programmed to:
        control the magnet system, the magnetic gradient system, and the RF system to image the human kidney to acquire MRI images of the entire human kidney, wherein contrast agents comprising cationized ferritin molecules are injected directly into vasculature of the human kidney, the contrast agents are configured to be bound with functioning glomeruli of the human kidney, the contrast agents cause signal magnitudes and phases of voxels of regions of the human kidney bound with the contrast agents to be different from signal magnitudes and phases of voxels of regions of the human kidney not bound with the contrast agents;
        derive intrarenal spatial distribution of measured MRI parameters within or between lobes of the human kidney, or within and between the lobes of the human kidney using the MRI images; and
        determine a function capacity of the human kidney based on the intrarenal spatial distribution to thereby nondestructively assess a renal allograft viability of the human kidney preserved for transplant; and
        generate a report of the function capacity of the human kidney.

2. The system as recited in claim 1, wherein the computer system is further programmed to measure an apparent volume of each of the functioning glomeruli, to count and estimate an apparent number of the functioning glomeruli, or both.

3. The system as recited in claim 1, wherein the contrast agents comprise apoferritin filled with at least one of a metal, a radio label, and a fluorescent molecule, and the apoferritin comprises cationic surface charge causing the apoferritin to target the functioning glomeruli.

4. The system as recited in claim 3, wherein the contrast agents comprise at least one of cationized ferritin and cationized modified ferritin.

5. The system as recited in claim 1, wherein the contrast agents comprise cationic charges that cause the contrast agents to be bound with the functioning glomeruli.

6. The system as recited in claim 1, wherein the computer system is further programmed to compare differences between signal magnitudes of first voxels in cortical structure and of second voxels in medullary structure.

7. The system as recited in claim 1, wherein the computer system is further programmed to:
derive characteristics of the MRI images; and
compare the characteristics of the MRI images with characteristics of images of healthy kidneys.

8. The system as recited in claim 7, wherein the computer system is further programmed to measure apparent volumes of the functioning glomeruli, wherein the characteristics comprise intrarenal distribution of the apparent volumes.

9. The system as recited in claim 7, wherein the computer system is further programmed to generate a line profile of signal magnitudes of voxels along a line in the MRI images, wherein the characteristics comprise spatial power spectrum of the line profile.

10. The system as recited in claim 1, wherein the computer system is further programmed to analyze the MRI images, to analyze a spatial distribution of glomeruli in the human kidney, to analyze a spatial distribution of the contrast agents in the human kidney, or any combination thereof.

11. The system as recited in claim 1, wherein the computer system is further programmed to analyze texture of the MRI images.

12. The system as recited in claim 1, wherein the computer system is further programmed to determine at least one of the functioning glomeruli and non-functioning glomeruli based on the MRI images.

13. The system as recited in claim 1, wherein the computer system is further programmed to determine at least one of a total perfused glomerular surface area, a total number of the functioning glomeruli, and an intrarenal distribution of glomerular volumes.

14. A magnetic resonance imaging (MRI) system, comprising:
a magnet system configured to generate a polarizing magnetic field about at least a portion of a subject arranged in the MRI system, wherein the subject comprises a preserved kidney;
a magnetic gradient system including a plurality of magnetic gradient coils configured to apply at least one magnetic gradient field to the polarizing magnetic field;
a radio frequency (RF) system configured to apply an RF field to the subject and to receive magnetic resonance (MR) signals therefrom;
a computer system programmed to:
control the magnet system, the magnetic gradient system, and the RF system to image the preserved kidney to acquire images of the preserved kidney, wherein the preserved kidney has lobes, contrast agents comprising functionalized ferritin molecules are directly injected into vasculature of the preserved kidney, the contrast agents comprise cationic charges that cause the contrast agents to be bound with functioning glomeruli of the preserved kidney, the contrast agents cause signal magnitudes and phases of voxels of regions of the preserved kidney bound with the contrast agents to be different from signal magnitudes and phases of voxels of regions of the preserved kidney not bound with the contrast agents;
derive intrarenal spatial distribution of at least one of glomeruli and nephrons within or between the lobes of the preserved kidney, or within and between the lobes of the preserved kidney using the images;
determine a function capacity of the preserved kidney based on the intrarenal spatial distribution to thereby nondestructively assess a renal allograft viability of the preserved kidney for transplant; and
generate a report of the function capacity of the preserved kidney for transplant.

15. The system as recited in claim 14, wherein the computer system is further programmed to measure an apparent volume of each of the functioning glomeruli, to count and estimate an apparent number of the functioning glomeruli, or both.

16. The system as recited in claim 14, wherein the contrast agents comprise at least one of cationized ferritin and cationized modified ferritin.

17. The system as recited in claim 14, wherein the computer system is further programmed to derive characteristics of the images and comparing the characteristics of the images with characteristics of images of healthy kidneys.

18. The system as recited in claim 17, wherein the computer system is further programmed to measure apparent volumes of the functioning glomeruli, wherein the characteristics comprise intrarenal distribution of the apparent volumes.

19. The system as recited in claim 17, wherein the computer system is further programmed to generate a line profile of signal magnitudes of voxels along a line in the images, wherein the characteristics comprise spatial power spectrum of the line profile.

20. The system as recited in claim 14, wherein the computer system is further programmed to analyze the images; to analyze a spatial distribution of glomeruli in the preserved kidney; to analyze a spatial distribution of the contrast agents in the preserved kidney; to determine at least one of the functioning glomeruli and non-functioning glomeruli based on the images; to determine at least one of a total perfused glomerular surface area, a total number of the functioning glomeruli, and an intrarenal distribution of glomerular volumes; or any combination thereof.

* * * * *